United States Patent [19]
Walton

[11] Patent Number: 5,864,291
[45] Date of Patent: *Jan. 26, 1999

[54] BREATHING MONITOR WITH ISOLATING COUPLER

[75] Inventor: Daniel G. Walton, Troy, Mo.

[73] Assignee: Lifetek, Inc., Troy, Mo.

[*] Notice: The term of this patent shall not extend beyond the expiration date of Pat. No. 5,400,012.

[21] Appl. No.: 350,834

[22] Filed: Dec. 7, 1994

Related U.S. Application Data

[63] Continuation of Ser. No. 46,034, Apr. 12, 1993, Pat. No. 5,400,012.

[51] Int. Cl.$^6$ .................................................. G08B 23/00
[52] U.S. Cl. ......................... 340/573; 340/663; 600/484; 600/534; 600/536; 600/561
[58] Field of Search .................................. 340/573, 665, 340/668; 600/484, 534, 390, 393, 508, 536, 561, 595; 1278/204.23, 716, 721

[56] References Cited

U.S. PATENT DOCUMENTS

| | | | |
|---|---|---|---|
| 3,268,845 | 8/1966 | Whitmore | 338/47 |
| 3,796,208 | 3/1974 | Bloice | 600/534 |
| 3,888,240 | 6/1975 | Reinhold, Jr. et al. | 600/390 |
| 4,250,434 | 2/1981 | Valansot | 315/362 |
| 4,296,757 | 10/1981 | Taylor | 600/534 |
| 4,359,726 | 11/1982 | Lewiner et al. | 340/666 |
| 4,392,126 | 7/1983 | Loyola | 340/573 |
| 4,450,437 | 5/1984 | Ho | 340/540 |
| 4,576,179 | 3/1986 | Manus et al. | 600/484 |
| 4,638,307 | 1/1987 | Swartout | 340/666 |
| 4,696,307 | 9/1987 | Montgieux | 600/534 |
| 4,846,462 | 7/1989 | Regnier et al. | 482/1 |
| 4,851,816 | 7/1989 | Macias et al. | 340/573 |
| 4,862,144 | 8/1989 | Tao | 340/572 |
| 4,884,067 | 11/1989 | Nordholm et al. | 340/686 |
| 5,304,984 | 4/1994 | Roldan | 340/573 |
| 5,400,012 | 3/1995 | Walton | 340/573 |

FOREIGN PATENT DOCUMENTS 2138144  10/1984  United Kingdom.

*Primary Examiner*—Benjamin C. Lee
*Attorney, Agent, or Firm*—Howell & Haferkamp, L.C.

[57] ABSTRACT

A breathing monitor for detecting SIDS in infants caused by apnea or the like includes an enclosure which is applied to a baby's torso with a strap. The enclosure is supported by and isolated from the baby's torso in its entirety by a fluid filled bladder coupler such that there is no direct contact between the enclosure and the baby's torso. A detector including a piezoelectric element is connected to the opposite side of the fluid coupler and a battery powered electronic circuit contained within the enclosure flashes an LED as the baby breathes and sounds an alarm should the baby fail to exhale for a predetermined time period. An adjustable strap connector for the strap provides visual indication of the strap being correctly applied and a limited range of permissible motion between the strap and enclosure as the baby breathes.

18 Claims, 2 Drawing Sheets

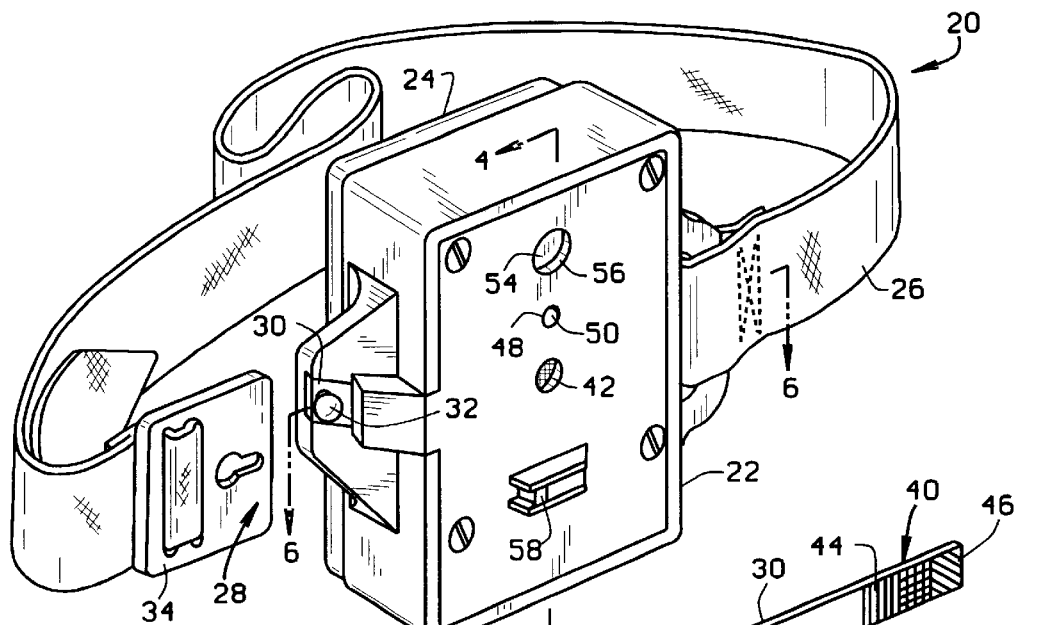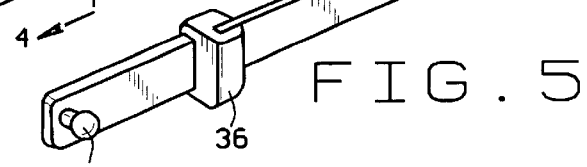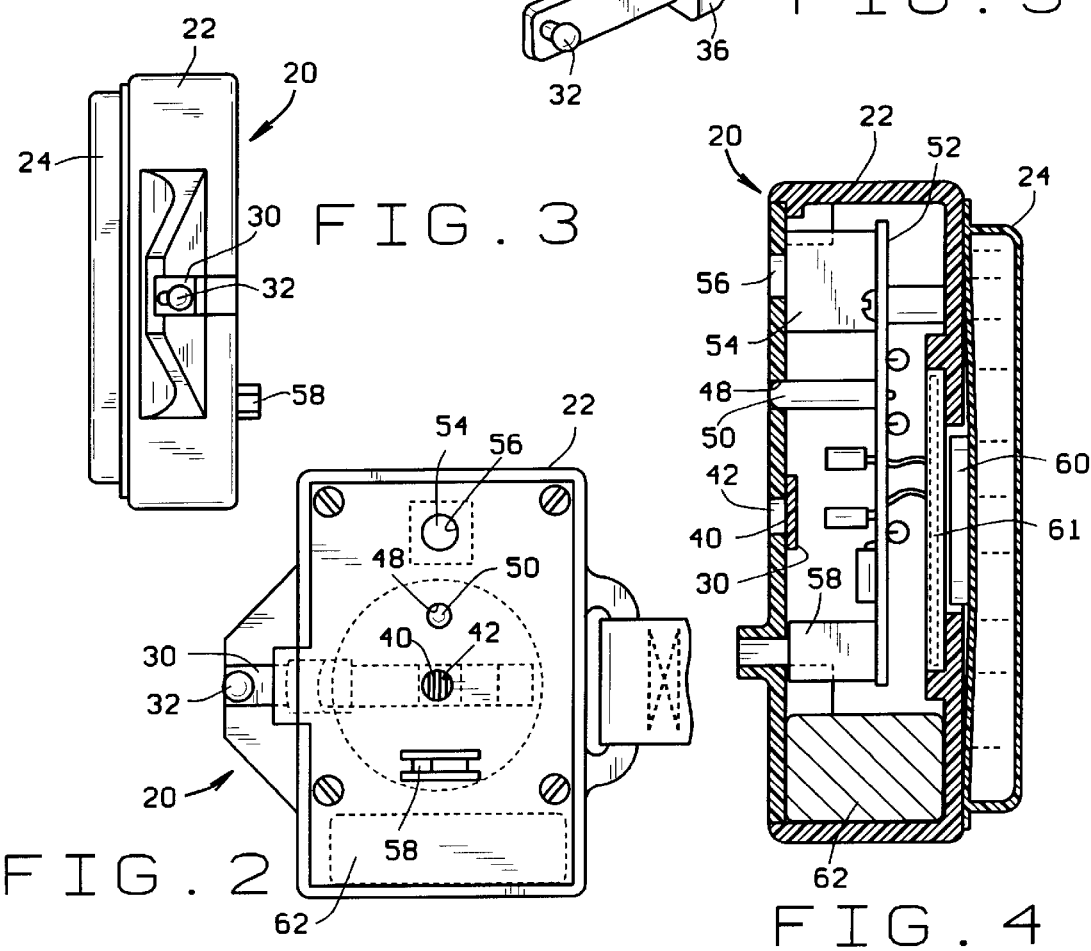

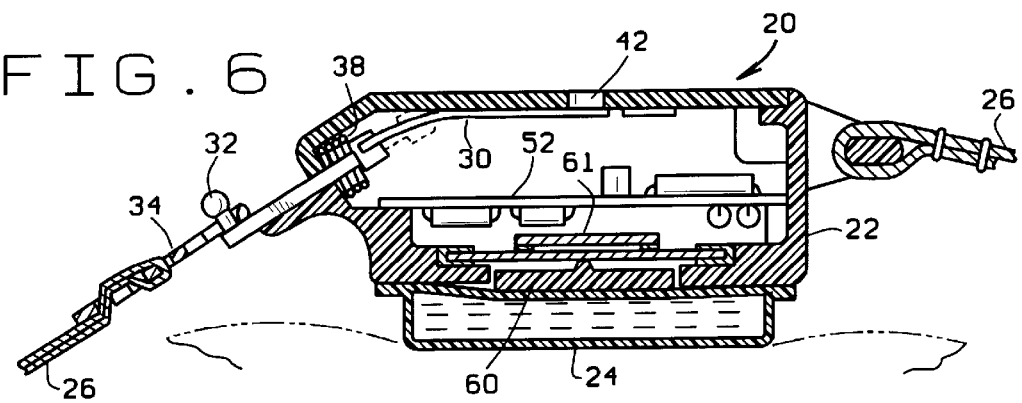
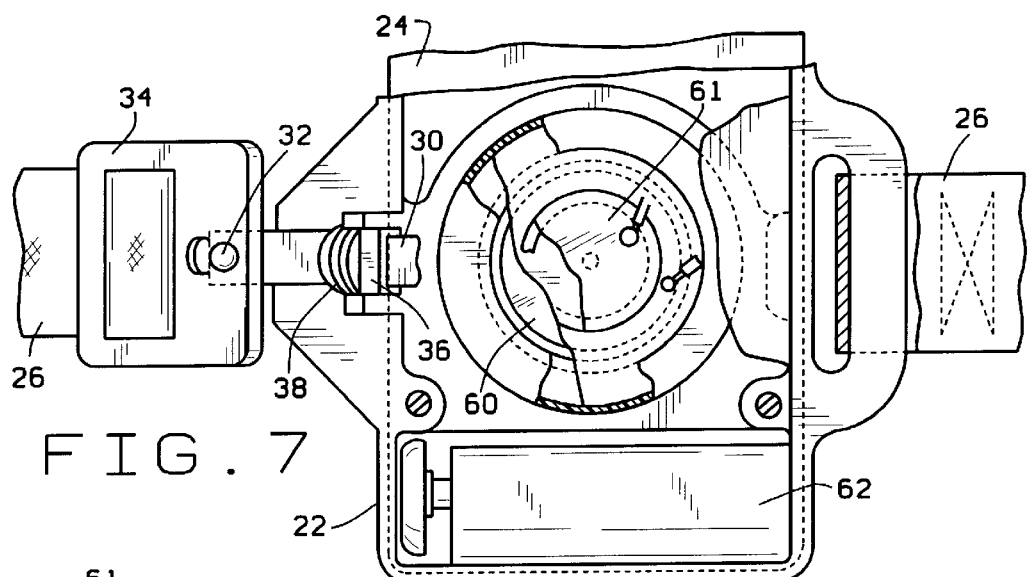
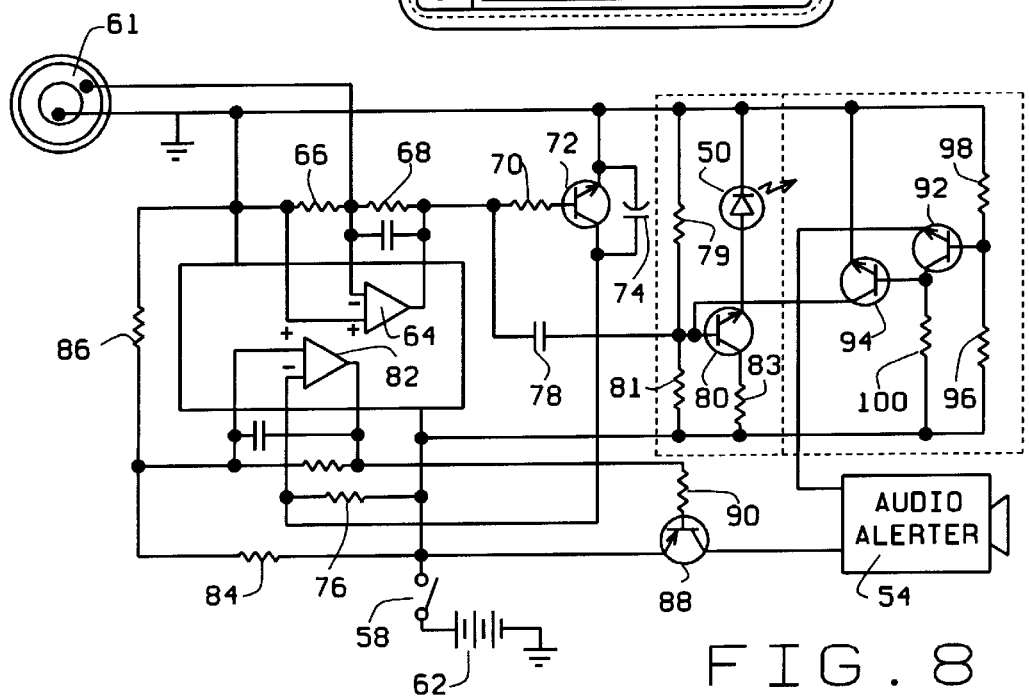

BREATHING MONITOR WITH ISOLATING COUPLER

This is a continuation of application Ser. No. 08/046,034, filed Apr. 12, 1993, U.S. Pat. No. 5,400,012.

BACKGROUND AND SUMMARY OF THE INVENTION

To a parent, the medical condition known as Sudden Infant Death Syndrome (SIDS) or apnea is a frightening specter which causes many a sleepless night. As is well known, SIDS is a major cause of death in babies and strikes unexpectedly and often with no warning symptoms. The only effective preventative is a surveillance of the infant. This surveillance has been achieved by parents essentially "standing guard" over their infants throughout the night in one extreme. To a lesser extent, parents have relied on other devices such as walkie talkies left in an open mike condition so that the parent may be reassured by the sound of the infant breathing. While hospitals have developed sophisticated and expensive devices which monitor infants in cribs, the inventor herein is not aware of any device which has been developed and is presently being marketed on a commercial scale of suitable design and cost for home use. While there have been many prior art attempts at such a device, none has been successful in solving this need. The device in the prior art which perhaps comes closest to achieving this is shown in U.S. Pat. No. 4,696,307. The device disclosed in the '307 patent is described as being a self-contained device which is strapped around the torso of a child, the device having an adhesive lining area for adhering it directly to the child's skin and a mechanical displacement transducer which is centrally located within the device such that as the belly of the child deflects upon the child's breathing, the mechanical actuator is actuated. An electronic circuit which monitors the transducer sounds an alarm if it determines that the child is not breathing. The '307 patent states that the adhesive portion of the box is essential for obtaining a significant response by the transducer as the baby's belly moves during breathing. This adhesive attachment provides a reference position and pressure against which the mechanical actuator works to produce a signal indicative of the baby's breathing.

Although the inventor herein has not attempted to test the device disclosed in the '307 patent, it is believed that there are significant disadvantages thereto. For example, proper application of the device to a baby, with the attendant adhesive attachment of the box to the baby's skin, must be quite time-consuming, uncomfortable for the baby, and unreliable in that untrained parents would generally be applying this device to their own baby. Furthermore, this device relies on a baby's belly moving in and out as a baby breathes. However, in some babies it is possible that the deflection of the belly is not as great as in other babies and there is no way to adjust the device for this required difference in sensitivity. While the '307 patent does suggest that ultrasound or hydraulic fluid could be used in place of the mechanical transducer, such would not eliminate the requirement that the device be adhered to the baby's stomach or that there be some pressure exerted on the baby's stomach which could very well be uncomfortable.

Perhaps most importantly, it is not clear to the inventor that the device in the '307 patent would reliably function. It is this concern which has probably interfered with the commercialization of this prior art device as there is certainly a long-felt need for such a device in order to avoid deaths of infants through SIDS.

In order to solve these and other problems in the prior art, the inventor herein has succeeded in designing and developing a breathing monitor which is self-contained, battery operated, includes an electronic circuit with an LED which flashes in response to each breath, an audio alarm in the event there are no breaths detected within a given preselected time period, and a fluid filled bladder coupler which interfaces between the entirety of the device and the baby in order to provide maximum sensitivity with minimal discomfort to the baby and, most importantly, reliable operation. A spring loaded tension adjuster type connector secures an end of an elastic strap to the device enclosure such that it may be snugly fastened about the baby and adjusted to within a proper operating range as indicated by a visual indicator to the parent, thereby affirming to the parent that it has been properly installed. This connector also provides for a limited amount of expansion and contraction, permitted through withdrawal and retraction of the connector from the device enclosure, to accommodate a baby's normal breathing. This further increases the comfort of the device as it is applied to a baby in that the '307 device does not provide for any such expansion or contraction. However, more importantly, this connector permits an inexperienced parent to reliably attach the device to his or her baby and be assured that the device is properly secured and will function properly. This is a major concern as parents must be assured that the device is properly installed in order that they may be relieved and not suffer the anxieties previously felt when no device was available.

As mentioned above, a fluid filled bladder coupler interfaces between the device enclosure and the baby. Unlike the device in the '307 patent, there is no direct contact between the device enclosure and, certainly, no adhesive contact required between the device enclosure and the baby's skin. As such, the present invention may be secured about a baby's night clothes or under garments and yet operate reliably as it responds to a change in tension in the elastic strap which secures the device enclosure to the baby. Furthermore, the invention may be applied to either the baby's back or belly and is not strictly limited to contact with the baby's belly as in the device in the '307 patent. This particular feature can be quite important because there is presently controversy with regard to the proper sleep position for babies in order to minimize the onset of SIDS. Some medical practitioners believe that babies should sleep on their backs which would accommodate application of the invention to a baby's belly while other practitioners believe that babies should sleep on their bellies which would require application of the invention to the baby's back. In either orientation, the present invention will work for the purposes intended.

The inventor has also solved the problem of indicating that the battery is losing its charge and needs to be replaced so that a parent can be assured that battery failure will not attribute to the failure to detect a baby's cessation of breathing in the middle of the night. By cleverly designing the electronic circuit, minimal power drain is achieved such that a single nine volt battery will provide continuous operation for many months. Secondly, the electronic circuit is designed so that an LED flashes as the baby breathes. If the battery is charged sufficiently such that the LED flashes as the baby is placed in its crib for sleep, the battery will have sufficient charge to last at least through that sleep period. Should the LED not flash as the monitor is strapped onto the child, then a parent will know that the battery has discharged dangerously low and needs to be replaced. Although this design provides fail-safe operation, it is anticipated that many parents will routinely replace the battery much more frequently due to the relatively low cost of the battery and their unfailing concern for the safety of their child. Nonetheless, in many cases, it is anticipated that a single nine volt battery will last sufficiently long to see the baby through the riskiest first year of life.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 1 is a perspective view of the breathing monitor and strap of the present invention;

FIG. 2 is a front view of the device enclosure;

FIG. 3 is a side view of the device enclosure;

FIG. 4 is a cross-sectional view taken along the plane of line 4—4 in FIG. 1 and detailing the interior mounting of the electronic circuit including LED, audio alarm, and battery;

FIG. 5 is a perspective view of the connecting rod which connects the strap end with the enclosure;

FIG. 6 is a partial cross-sectional view taken along the plane of line 6—6 detailing the application of the device around a baby's torso;

FIG. 7 is a top view partially broken away to detail the piezoelectric detector mounted within the enclosure; and FIG. 8 is a schematic diagram of the electronic circuit enclosed within the device.

DETAILED DESCRIPTION OF THE PREFERRED EMBODIMENT

As shown in FIG. 1, the breathing monitor 20 of the present invention includes a device enclosure 22 with a fluid filled bladder coupler 24 secured to and substantially covering one side thereof and an elastic strap 26 which is affixed at one end of enclosure 22 with an adjustable connector 28 at the other end thereof for adjustably securing it to the opposite side of the enclosure 22. The adjustable connector 28 includes the push rod 30 as best shown in FIG. 5 which has a post 32 to which the buckle attachment 34 on strap 26 is secured, a shoulder 36 which compresses spring 38 (see FIG. 6) against an interior wall of enclosure 22 as the strap 26 is tightened about a baby's torso. A central color coded area 40 on push rod 30 is viewable through a window 42 of enclosure 22 (see FIGS. 1 and 6) which indicates to a parent that the strap 26 has been correctly secured about the baby's torso such that spring 38 is compressed to a correct operating range for proper operation of the breathing monitor 20. Color coded area 40 is surrounded by a pair of secondary color coded areas 44, 46 which indicate, if viewable through window 42, that the strap 26 is either too loose or too tight and should be readjusted. This tension adjustment ensures proper installation and use by a parent of the breathing monitor 20. Furthermore, this adjustable connector 28 provides for a limited amount of expansion and contraction of the strap 26 about the baby's torso as the baby breathes in order to ensure the comfort of the baby.

As shown in FIGS. 2, 4, 6 and 7, the interior of enclosure 22 also provides an opening 48 through which an LED 50 is viewable to indicate, as it flashes, that the baby is breathing and that the battery is charged. The electronic circuit (see FIG. 8) is mounted on a PC board 52, including LED 50, and is supported within the enclosure 22, as is well known in the art. An audio alerter 54 is oriented adjacent still another opening 56 in enclosure 22 in order to announce an alarm in the event that the baby's breathing is not detected. An on/off switch 58 is mounted on PC board 52 and extends through an opening in enclosure 22 for turning the breathing monitor 20 on or off, as desired. A force concentrator 60 impinging on a piezoelectric element 61, to achieve maximum bending force on the piezoelectric element 61, comprises a detector and is mounted to the back of enclosure 22 and is in direct contact with the fluid filled bladder coupler 24 which rests against the baby's torso. It is noted that the fluid filled bladder coupler 24 extends along essentially the entirety of the backside of the enclosure 22 and is in direct contact not only with force concentrator 60 but also the enclosure 22 as well. Thus, fluid filled bladder coupler 24 supports or isolates the entirety of the enclosure 22 from the baby's torso, except for the strap 26 which surrounds the torso. A nine volt battery 62 or the like is conveniently contained in enclosure 22 and powers the electronic circuit as shown in FIG. 8.

Turning now to the electronic circuit as shown in FIG. 8, a first op amp 64 has its positive input connected to ground and one side of piezoelectric element 61 and its negative input connected to the other side of piezoelectric element 61, with a resistor pair 66, 68 being used to set its gain. As the piezoelectric element 61 is actuated by the baby's exhaling against force concentrator 60, op amp 64 produces a pulse which is applied through resistor 70 to transistor 72 which shunts capacitor 74. As capacitor 74 is part of an RC circuit including resistor 76 having a time constant of 35 seconds, the baby's exhaling continuously resets this time delay unless a period of greater than 35 seconds passes without a breath being taken. To achieve maximum sensitivity, the piezoelectric element 61 is connected in polarity to reset the time delay as the baby exhales rather than on inhale as the inventor has found the act of exhaling to be a more abrupt movement. A pulse from op amp 64 also passes through capacitor 78 to turn on transistor 80 which pulses LED 50 to provide a visual indication that the baby has exhaled. A resistor bridge 79, 81 biases transistor 80 just below its turn on point to adjust the sensitivity of transistor 80 to the pulse generated by op amp 64. Also, resistor 83 limits the current through LED 50, as known in the art.

A second op amp 82 has its positive input biased to a set voltage by a pair of resistors 84, 86. If the voltage across capacitor 74 charges above this set voltage, then the output of op amp 82 goes negative which is applied to the base of transistor 88 by resistor 90 to thereby turn it on and actuate audio alerter 54 to indicate to a parent that the baby has not taken a breath for the 35 second time constant.

Transistors 92, 94 act as a low battery voltage indicator circuit. A pair of resistors 96, 98 bias transistor 92 on until battery voltage drops below a nominal eight volts. At that point, transistor 92 turns off which permits transistor 94 to turn on with base current through resistor 100. With transistor 94 being turned on, base current to transistor 80 is shunted therefrom, thereby turning off transistor 80 and disabling LED 50 from being flashed. Thus, should a parent strap the breathing monitor 20 around a baby's torso and, while watching the baby breathe, the LED 50 fails to flash, the parent knows immediately that the battery needs to be replaced. Alternately, if the LED 50 is flashing, the battery is adequate and the parent may be assured that it is functioning properly.

The inventor has found that the fluid filled bladder coupler 24 with force concentrator 60 and piezo-electric element 61 is incredibly sensitive. The fluid filled bladder coupler 24 may be filled with any sterile fluid, the inventor having used saline in a prototype. However, it is anticipated that any fluid, gel, or the like which provides a "soft" coupling might just as well be used and perform satisfactorily. As previously noted, fluid filled bladder coupler 24 supports the entirety of the enclosure 22 from the baby's torso, and there is no direct contact between the enclosure 22 and the baby's torso. This effectively isolates the enclosure 22 and dramatically increases the sensitivity. This provides tremendous advantages in not only sensing the breathing motion of the baby, but also in providing comfort to the baby to minimize interference with the baby's sleep. This comfort and sensitivity is enhanced by the adjustable tension connector between the strap and enclosure which permits a limited amount of deflection of the elastic strap with respect to the enclosure as the baby breathes. These features enhance the operation of the present invention.

While the description of the preferred embodiment of the invention details its use with a baby, the invention also has utility with people of any age and even an animal such as a dog. In some veterinary procedures, it is desirable to monitor the breathing of an animal. For example, as a dog is being operated on and while it is recovering from any anesthesia it would be desirable to use the invention to ensure that any interruption in breathing is corrected. Such other uses are intended to be covered by the claims appended hereto.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. In a device for monitoring the breathing of a subject, said device being self-contained within an enclosure and including a strap for wrapping around said subject to thereby secure said enclosure to said subject, the improvement comprising a coupler solely isolating said enclosure from said subject, said coupler providing the sole support for said enclosure from said subject other than said strap.

2. The device of claim 1 further comprising an adjustable connector between said strap and said enclosure, said connector having means for permitting said strap to retract and withdraw within a limited range.

3. The device of claim 2 wherein said adjustable connector has a spring tension adjuster so that said strap may be adjusted to properly be within a predetermined tension range about said subject.

4. The device of claim 3 wherein said spring tension adjuster has an indicator for displaying the tension to which said connector has been adjusted to thereby facilitate the proper adjustment thereof as said device is applied to a subject.

5. The device of claim 1 wherein said enclosure includes a detector, said coupler being positioned to interface between said detector and said subject.

6. The device of claim 5 wherein said coupler also interfaces between parts of said enclosure other than said detector and said subject.

7. The device of claim 5 wherein said device includes an alarm and means for sounding said alarm upon failure of said device to detect the breathing of said subject after a predetermined time delay.

8. The device of claim 7 wherein said device includes an indicator for indicating each time the detector detects that the subject breathes.

9. The device of claim 7 wherein said device includes a battery connected to said alarm and said alarm sounding means, and means for indicating when said battery has discharged below a predetermined charge level.

10. The device of claim 9 wherein said device includes an electronic circuit connected to said alarm.

11. The device of claim 10 wherein said electronic circuit is interconnected between said detector and said indicator and further comprises means for actuating said indicator in response to said detector.

12. In a device for monitoring the breathing of a subject, said device being self-contained within an enclosure and including a strap for wrapping around said subject to thereby secure said enclosure to said subject, the improvement comprising a coupler for isolating and supporting said enclosure from said subject, said enclosure not being in supporting contact with said subject.

13. The device of claim 12 wherein said device includes a detector mounted in said enclosure and in contact with said coupler so that said coupler transmits any impact force to said detector.

14. The device of claim 13 wherein said coupler is in direct contact with and supports both of said detector and said enclosure from said subject.

15. The device of claim 14 further comprises an electronic circuit contained within said enclosure and connected to said detector, an LED connected to said electronic circuit, an audio alarm connected to said electronic circuit and a battery connected to said electronic circuit for powering said device so that as said detector is actuated through said coupler by said subject said electronic circuit causes said LED to flash, and if said detector is not actuated within a predetermined time period said electronic circuit sounds said audio alarm.

16. In a device for monitoring the breathing of a subject, said device being self-contained within an enclosure and including a strap for wrapping around said subject to thereby secure said enclosure to said subject, the improvement comprising an adjustable tension connector for connecting said strap to said enclosure so that said strap may be adjusted to be within a predetermined tension range about said subject, said connector having a mechanical linkage for permitting said strap to withdraw and retract within a limited range, and an indicator for visually displaying the relative degree of tension to which said connector has been adjusted.

17. The device of claim 16 wherein said adjustable tension connector includes a spring, and wherein said indicator includes a plurality of different available indications available for display.

18. The device of claim 17 wherein said plurality of different available indications includes at least one indicating a range of tensions acceptable for proper operation for said breathing monitor.

* * * * *